US010385842B2

(12) United States Patent
Kuczek et al.

(10) Patent No.: US 10,385,842 B2
(45) Date of Patent: Aug. 20, 2019

(54) LIMITER FOR A DISPENSING DEVICE

(75) Inventors: John Kuczek, Lowell, MA (US); Clive Patience, Georgetown, MA (US); Donovan Quinn, Cambridge, MA (US); Lucio Giambattista, East Hanover, NJ (US)

(73) Assignees: Biogen MA Inc., Cambridge, MA (US); SHL Group AB, Nacka Strand (SE)

( * ) Notice: Subject to any disclaimer, the term of this patent is extended or adjusted under 35 U.S.C. 154(b) by 613 days.

(21) Appl. No.: 14/113,963

(22) PCT Filed: Apr. 16, 2012

(86) PCT No.: PCT/US2012/033739
§ 371 (c)(1),
(2), (4) Date: Feb. 21, 2014

(87) PCT Pub. No.: WO2012/148717
PCT Pub. Date: Nov. 1, 2012

(65) Prior Publication Data
US 2014/0180217 A1    Jun. 26, 2014

Related U.S. Application Data

(60) Provisional application No. 61/479,957, filed on Apr. 28, 2011.

(51) Int. Cl.
*A61M 5/315* (2006.01)
*F04B 49/14* (2006.01)
*B65D 83/00* (2006.01)

(52) U.S. Cl.
CPC ......... *F04B 49/14* (2013.01); *A61M 5/31501* (2013.01); *A61M 5/31536* (2013.01); *B65D 83/0033* (2013.01); *A61M 5/31591* (2013.01)

(58) Field of Classification Search
CPC .......................... F04B 49/14; B65D 83/0033; A61M 5/31501; A61M 5/31536; A61M 5/31591
See application file for complete search history.

(56) References Cited

U.S. PATENT DOCUMENTS 772,114 A * 10/1904 Pappenheim ..... A61M 5/31501
604/220
4,357,971 A    11/1982 Friedman
(Continued)

FOREIGN PATENT DOCUMENTS

EP    0 904 792 A2    3/1999
EP    1 702 636 A1    9/2006
(Continued)

OTHER PUBLICATIONS

Merriam-Webster Dictionary definition for "integrally" available online at https://www.merriam-webster.com/dictionary/integrally (accessed Sep. 5, 2018).*

*Primary Examiner* — Amber R Stiles
(74) *Attorney, Agent, or Firm* — Wolf, Greenfield & Sacks, P.C.

(57) ABSTRACT

A limiter for a dispensing device is provided. The limiter includes a body (20) arranged to mount with at least a portion of a dispensing device (300), and a stop extending from the body. The stop (40) is configured to permit movement a plunger of the dispensing device a predetermined distance in a dispensing direction correlated to a desired volume of medium to be delivered from the dispensing device. The stop is configured to prevent further movement of the plunger in the dispensing direction, thereby limiting the amount of medium delivered from the dispensing device. The dispensing device may be a syringe.

18 Claims, 6 Drawing Sheets

(56) References Cited

U.S. PATENT DOCUMENTS

| | | | |
|---|---|---|---|
| 5,951,526 A * | 9/1999 | Korisch | A61M 5/3129 |
| | | | 604/208 |
| 5,975,355 A | 11/1999 | Cecala et al. | |
| 2004/0162528 A1 * | 8/2004 | Horvath | A61M 5/31548 |
| | | | 604/207 |

FOREIGN PATENT DOCUMENTS

| | | |
|---|---|---|
| JP | 2006-517844 | 8/2006 |
| JP | 2008-532665 | 8/2008 |

\* cited by examiner

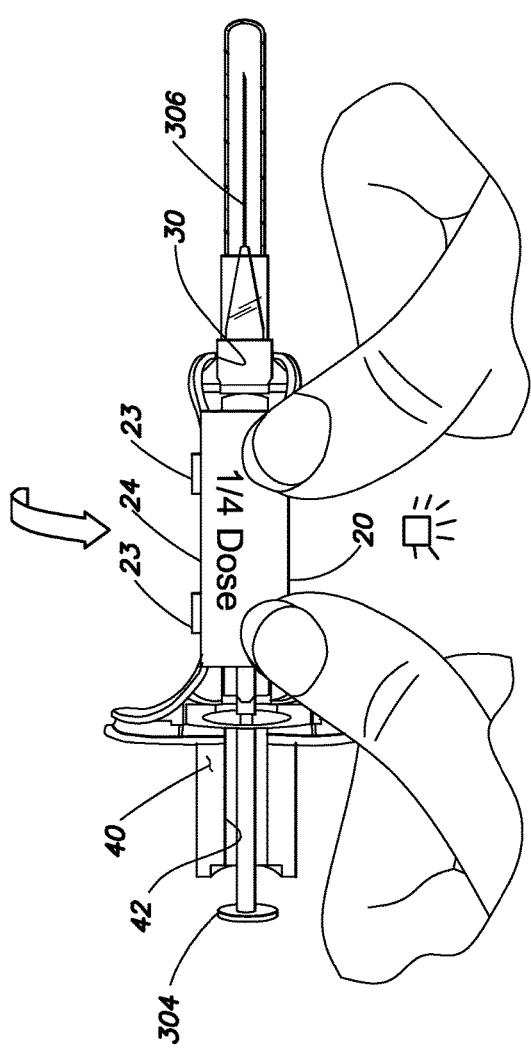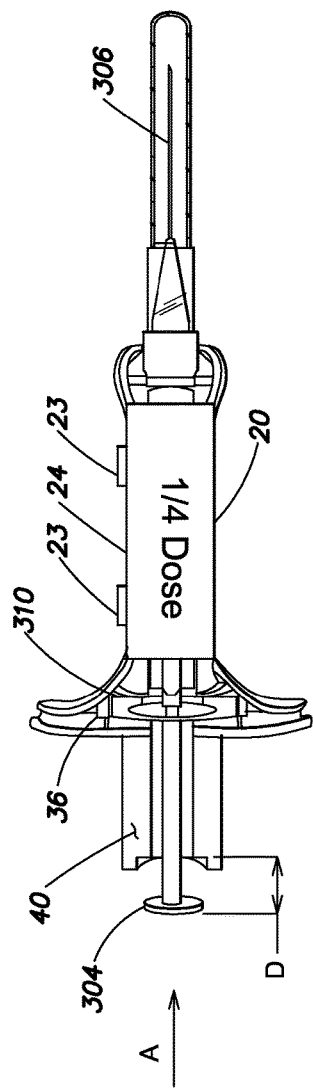

LIMITER FOR A DISPENSING DEVICE

RELATED APPLICATIONS

This application is a National Phase Application under 35 U.S.C. § 371 of International Application No. PCT/US2012/033739, filed Apr. 16, 2012, which claims the benefit under 35 U.S.C. § 119(e) of U.S. provisional patent application, Ser. No. 61/479,957, filed Apr. 28, 2011, the contents of both of which are incorporated herein by reference in their entirety.

FIELD

The present invention is directed to a limiter for a dispensing device, and more particularly to a limiter which limits the amount of medium delivered from a dispensing device, such as a syringe.

BACKGROUND

Medications are often dispensed to a patient via a dispensing device, such as a syringe. The syringe generally includes a barrel which holds the medication, a needle attached to one end of the barrel to inject the medication into the patient, and a plunger slideably received within the other end of the barrel to push the medication out of the barrel and into the needle.

Many medications are packaged in prefilled syringes. In a prefilled syringe, the syringe barrel is filled with a full dose of the medication. The needle of the prefilled syringe is typically covered and/or replaced with a safety cap. To dispense the medication, the needle is attached to the end of the barrel and/or the safety cap is removed from the needle and the needle is inserted into the patient. The patient or caregiver slides the plunger through the barrel of the syringe until all of the medication is injected.

There are circumstances in which the patient does not need, or should not receive, a full dose of the medication in a prefilled syringe. For example, when a patient is starting a new medication, a doctor may recommend beginning with a partial dose to help the patient adapt to the medication. This approach is known as titration. To administer a partial dose, the patient is instructed to partially slide the plunger through the barrel. The syringe barrel may include graduated markings which the patient may use as a reference when dispensing a partial dose.

SUMMARY

In one illustrative embodiment, a limiter for a dispensing device is provided. The limiter includes a body arranged to mount with at least a portion of a barrel of a dispensing device, and a stop extending from the body. The stop is configured to permit movement of a plunger of the dispensing device a predetermined distance in a dispensing direction correlated to a desired volume of medium to be delivered from the dispensing device. The stop is configured to prevent further movement of the plunger in the dispensing direction, thereby limiting the amount of medium delivered from the dispensing device.

In another illustrative embodiment, a kit is provided where the kit includes a plurality of limiters. The stop of the first limiter is configured to permit movement of the plunger a first predetermined distance in the dispensing direction, and the stop of the second limiter is configured to permit movement of the plunger a second predetermined distance in the dispensing direction, where the first predetermined distance is greater than the second predetermined.

In yet another embodiment, a method of limiting the dispensing of liquid from a dispensing device. The method includes mounting a dispensing device with a limiter such that at least a portion of the dispensing device is mounted with a body of the limiter, where a stop extends from the body. The method also includes moving a plunger of the dispensing device a predetermined distance in a dispensing direction correlated to a desired volume of medium to be dispensed, to dispense the medium until the plunger contacts the stop that is configured to prevent further movement of the plunger in the dispensing direction, thereby limiting the amount of medium delivered from the dispensing device.

Various embodiments of the present invention provide certain advantages. Not all embodiments of the invention share the same advantages and those that do may not share them under all circumstances.

Further features and advantages of the present invention, as well as the structure of various embodiments that incorporate aspects of the invention are described in detail below with reference to the accompanying drawings.

BRIEF DESCRIPTION OF DRAWINGS

The foregoing and other objects and advantages of the invention will be appreciated more fully from the following drawings, wherein like reference characters designate like features, in which:

FIGS. 3-6 are schematic perspective views of a syringe being inserted into the device of FIG. 2;

DETAILED DESCRIPTION

Applicant recognized that it may be difficult to accurately dispense an amount of medium from a dispensing device. For example, when the patient is self-injecting with a syringe, it may be difficult for the patient to look at markings on the side of the syringe barrel to estimate the desired partial dose. Such difficulties may lead to either an under dose or an overdose of the medication. As mentioned above, when a new medication is being administered, dispensing more than a recommended partial dose may lead to undesirable side effects. Dispensing less than the desired partial dose may diminish the effect of the medication. Applicant recognized a need for a device to help alleviate these difficulties.

Aspects of the present invention are directed to a limiter configured to limit the amount of medium delivered from a dispensing device. As set forth in greater detail below, the limiter may be configured to dispense a desired partial dose of the medium. Although the following description describes such a limiter in connection with a syringe, it is also contemplated that the limiter may be used with other dispensing devices that dispense medication. Furthermore, although the following description describes the dispensing device having a needle which is used to inject the medium into a patient, a needle is not required in all embodiments.

It is contemplated that the medium may be expelled from the dispensing device without being injected into a patient with a needle. For example, the medium may be configured to be expelled and either ingested or inhaled (via a patient's nose or mouth).

It is also contemplated that the limiter may be used in connection with a variety of types of medium which may be dispensed from the dispensing device. For example, in one embodiment, the limiter is for use with dispensing devices which dispense medication. One of skill in the art would appreciate that the medication may, for example, be in liquid form, gaseous form, and/or a solid form (such as a powder form). It should also be recognized that the limiter may be used to limit the dispensing of other non-medication substances, as the invention is not so limited.

Furthermore, it is contemplated that the limiter may be configured in a manner for easy handling. The limiter may be configured for use with a medication that is given to a patient with deteriorating manual dexterity. Thus, it may be difficult for the patient both to handle small components as well as to hold the dispensing device. As set forth below, in one embodiment, the limiter is configured with larger components and with a finger grip to permit easier handling.

Figure 1:
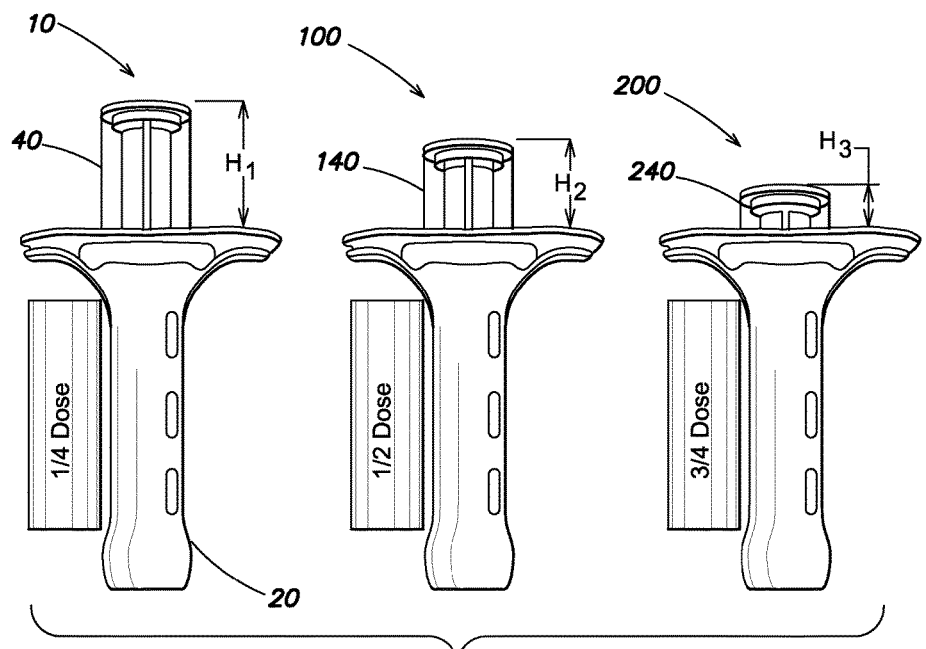
FIG. 1 is a schematic view of a kit including three different sized syringe dispensing devices.

Turning now to the figures, FIG. 1 illustrates a kit which includes a plurality of limiters 10, 100, 200. In this particular embodiment, a first limiter 10 is configured to dispense only one quarter of the medium in the dispensing device, a second limiter 100 is configured to dispense one half of the medium in the dispensing device, and a third dispensing device 200 is configured to dispense three quarters of the medium in the dispensing device. As discussed below, the kit may be arranged with limiters which may be used to dispense incrementally increasing doses of the medium. It should be recognized that, in another embodiment, a limiter 10, 100, 200 may be configured to dispense a different amount of the medium in a dispensing device, including, but not limited to one third, two thirds, and a full dose. It should be recognized that when multiple limiters are provided, the volume change between the doses need not be uniform. The details of the first limiter 10 are discussed in greater detail below. The second and third limiters 100, 200 may include similar components.

As shown in FIGS. 2-5, the limiter 10 is configured to limit the amount of medium dispensed from a dispensing device 300. In this particular embodiment, the dispensing device is a syringe. The limiter 10 includes a body 20 arranged to mount with at least a portion of a dispensing device 300. In this illustrative embodiment, the body 20 is arranged to mount with a barrel 302 of the dispensing device 300. As shown, the body 20 may include a slot 36 which is configured to mount with a flange portion 310 of the dispensing device 300. The slot 36 may be sized and arranged to receive the flange 310.

Figure 4:
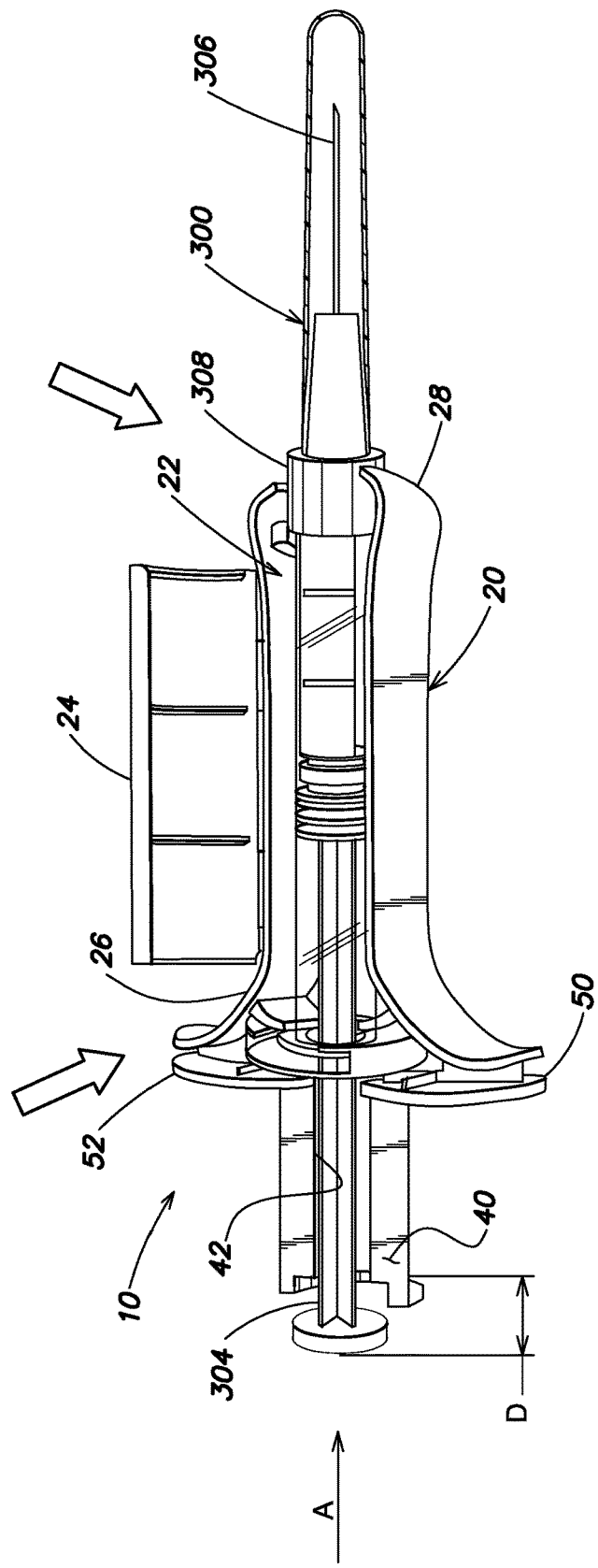
Figure 7:
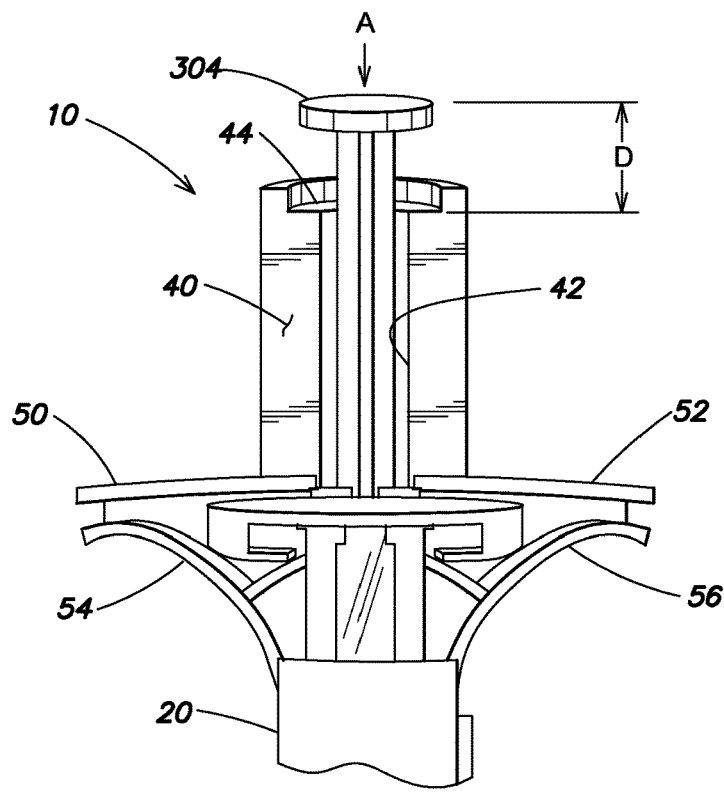
FIG. 7 is a detailed view of a portion of the device of FIG. 2.
Figure 8:
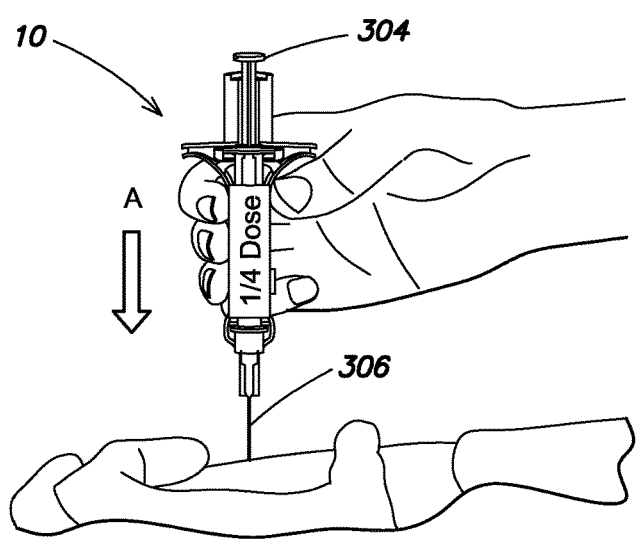
FIGS. 8-10 are schematic perspective views illustrating the device of FIG. 2 being used to dispense liquid from a syringe into a patient.
Figure 9:
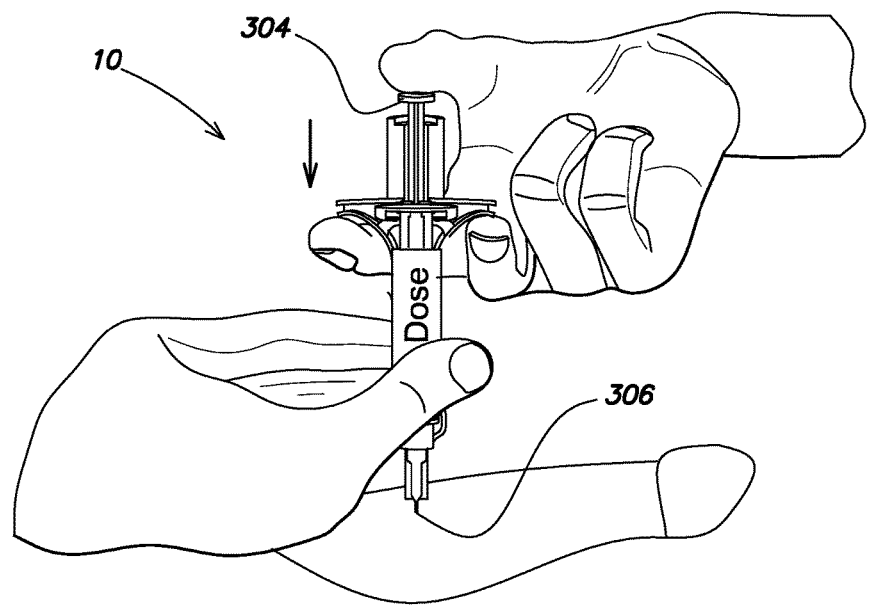
Figure 10:
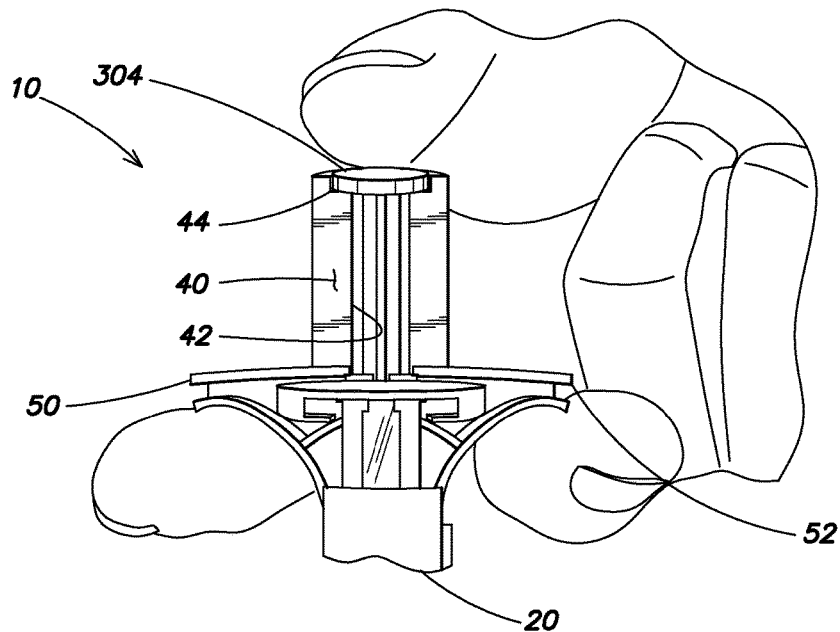

A stop 40 extends from the body 20 and as set forth below, the stop 40 is configured to limit the amount of medium dispensed by limiting the stroke length of the plunger 304 of the dispensing device. As shown in FIGS. 4, 6 and 7, the stop 40 permits movement of a plunger 304 of the dispensing device 300 a predetermined distance D in a dispensing direction (see arrow A) which is correlated to the desired volume of medium to be delivered from the dispensing device 300. As illustrated, the stop 40 is configured to prevent further movement of the plunger 304 in the dispensing direction A, thereby limiting the amount of medium delivered from the dispensing device.

In the illustrative embodiment, the body 20 is a housing which is configured to hold at least a portion of a syringe barrel 302 and the stop 40 is configured as a collar extending outwardly from the first end 26 of the housing. The collar may have a channel 42 configured to receive at least a portion of a plunger 304 such that the plunger 304 is movable within the channel 42. In this particular embodiment, the second end 28 of the housing has an opening 30 such that a needle 306 coupled to the barrel 302 extends out of the housing.

The housing may include a receptacle 22 and a door 24. In this illustrative embodiment, the door 24 is pivotally coupled to the receptacle 22 via hinges 23. The door may be opened to place the dispensing device 300 within the housing, and the door is pivoted closed to retain the dispensing device within the receptacle 22. As shown, the door may include a plurality of protrusions which may mate within corresponding components in the receptacle 22 to lock the door in the closed position. In another embodiment, the door 24 may be slidably coupled to the receptacle, and in yet another embodiment, the housing may not include a door, as the invention is not so limited. As shown, the housing may enclose a substantial portion of the barrel 302. However, it is also contemplated that the housing may be configured differently, and may, for example, include one or more openings such that the barrel 302 is more visible when the dispensing device 300 is in the limiter 10.

In one embodiment, the door 24 is provided to visually obstruct a substantial portion of the barrel 304 of the dispensing device 300. After a partial dose is administered to a patient, some of the medication remains in the barrel 304. There is a concern that a patient will try to reuse this medication. Reuse of the dispensing device 300 may compromise the sterility of the medication which could potentially lead to infection. Thus, the door 24 may be provided to cover the remaining medication so that a patient may be less likely to reuse the device 300.

It should be appreciated that although the housing and collar are discussed above, it is also contemplated that the body 20 and stop 40 may be arranged differently, as the invention is not so limited.

As shown in FIGS. 7-10, the limiter 10 is configured such that a partial dose of the medium in the dispensing device 300 can be accurately delivered to a patient. In particular, the limiter 10 is configured such that the plunger 304 is movable into the barrel 302 to push medium into the needle 306 so that the liquid can be expelled from the device 300. The stop 40 is arranged to permit movement of the plunger 304. The stop 40 may be positioned to provide the desired partial dose of the liquid and is arranged to prevent further movement of the plunger 304. In this respect, the plunger 304 may be movable into the barrel 302 of the dispensing device 300 to push a partial dose of the medium into the needle 306. Once the plunger 304 contacts the stop 40, further movement of the plunger 304 is prevented which prevents further medium from being dispensed. One of skill in the art will appreciate that by varying the height $H_1$ of the stop 40, one can control the predetermined distance D that the plunger 304 is permitted to travel in the dispensing direction A to dispense the medium, thus dispensing a controlled partial dose.

In this particular illustrative embodiment, the stop has an end wall which may be recessed to form a socket 44 configured to contact an end portion of the plunger 304 to prevent further movement of the plunger in the dispensing direction. In this illustrative embodiment, the collar is substantially C-shaped and the socket is substantially C-shaped. However, it should be appreciated that other shapes and configurations are also contemplated, as the invention is not so limited. For example, square, oval, triangular and irregular shapes are also contemplated. In this illustrative embodiment, the outer shape of the stop 40 is substantially the same as the shape of the socket 44. The invention also contemplates embodiments where the shape of the stop 40 is different than the shape of the socket 44.

Other stop configurations are also contemplated as the invention is not limited to the collar configuration shown in the figures. For example, in one embodiment, the stop 40 may include one or more protrusions extending from the body 20 designed to interfere with the movement of the plunger 304. One of skill in the art would appreciate that the stop 40 may include any feature which blocks or inhibits further movement of the plunger 304 once the plunger 304 contacts the stop 40.

Furthermore, an adjustable stop 40 may be provided. The stop 40 may be adjustable to adjust the amount of the medium that can be dispensed from the dispensing device 300 with one particular limiter 10. As mentioned above, the stop 40 is configured to permit movement of the plunger 304 a predetermined distance D which is correlated to a desired volume of medium to be delivered. The height $H_1$ of the stop 40 may be adjustable to vary the predetermined distance D that the plunger can move. For example, the stop 40 may include telescoping portions. One of ordinary skill in the art would appreciate that there are a variety of ways in which the stop 40 may be adjustable.

Figure 2:
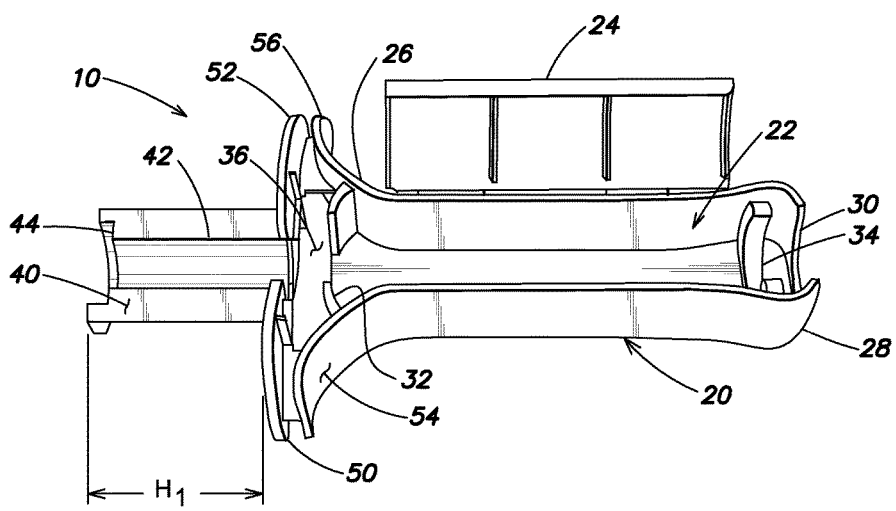
FIG. 2 is a schematic perspective view of one embodiment of a syringe dispensing device.
Figure 3:
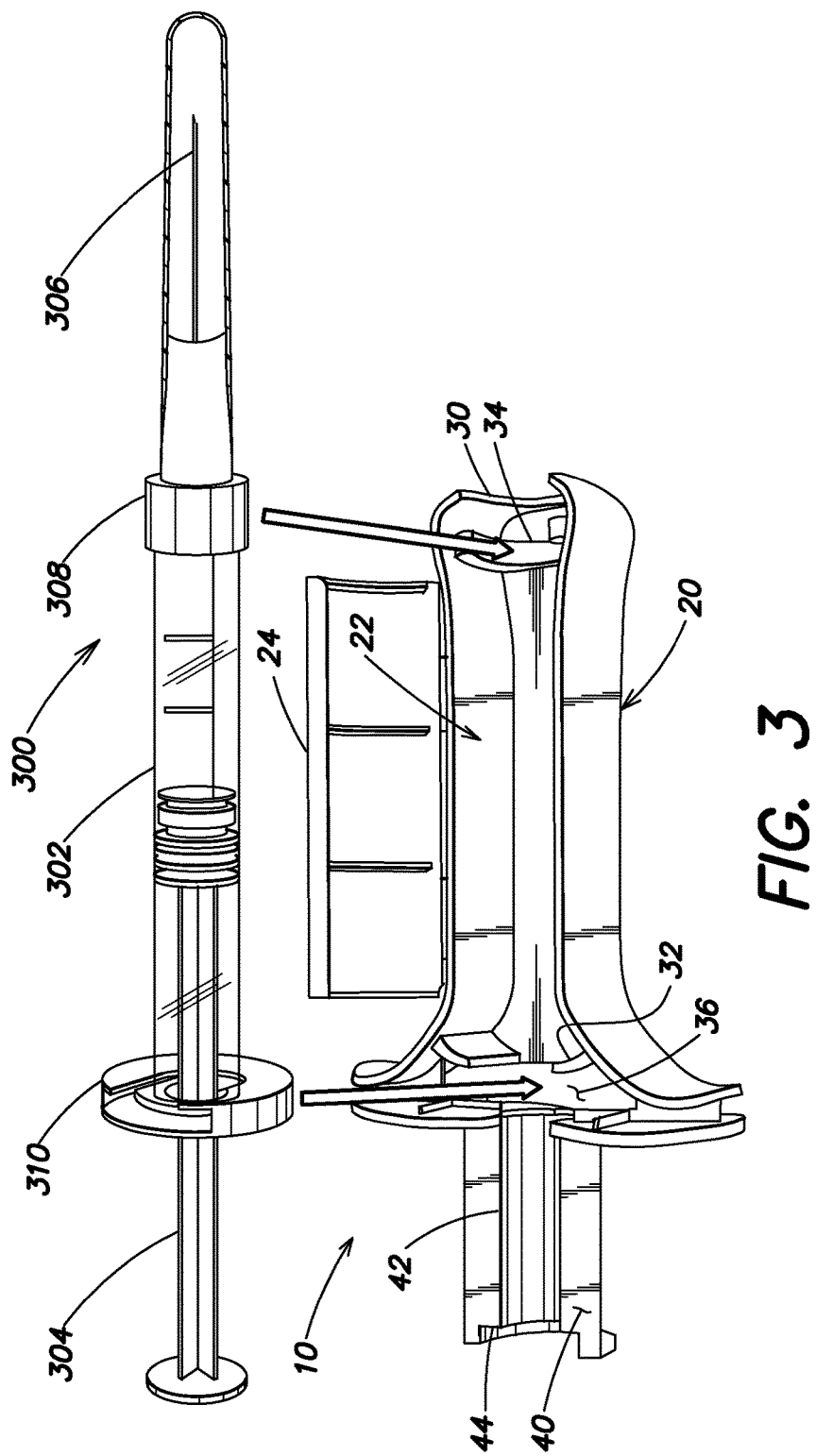

As shown in FIGS. 2-4, the housing may include at least one rib 32, 34, configured to position and/or retain the barrel 302 of the dispensing device within the housing. In one illustrative embodiment, the housing includes a first rib 32 positioned at a first end 26 of the housing. This rib 32 may be positioned within the receptacle 22 and may be configured to engage with an upper portion of the barrel 302. The rib 32 may be resilient such that it can flex to provide a snap-fit arrangement of the dispensing device 300 within the housing.

A second rib 34 may be positioned at the second end 28 of the housing. As illustrated, the second rib 34 may be positioned within the receptacle near the opening 30 and may be configured to engage with a lower portion of the barrel 302 of the dispensing device 300. In one embodiment, the second rib 34 is substantially C-shaped to align with the outer contour of the barrel. As shown in FIGS. 3-4, the lower portion of the barrel 302 may include a flange 308 configured to couple the barrel 302 to the needle 306 of the dispensing device. The second rib 34 may be configured to be smaller than the outer diameter of the flange 308 to prevent the needle 306 from sliding into the housing.

The limiter 10 may also include one or more components configured to provide a finger grip during dispensing. As mentioned above, such finger grips may enhance the handling of the dispensing device. In one illustrative embodiment, the body 20 includes at least one outwardly extending arm 50, 52 arranged to provide a finger grip during dispensing. In this illustrative embodiment, there are two arms 50, 52 positioned at the first end 26 of the housing, and the underside 54, 56 of each of the arms 50, 52 has a curved contour to match the profile of a finger tip.

The limiter 10 may be used as follows: At least a portion of the dispensing device 300 may be mounted with the body 20 of the limiter 10. If the limiter includes a door 24, the door may be opened to facilitate the placement of the device 300 relative to the limiter, and the door 24 may thereafter be closed. If the limiter includes one or more ribs 32, 34, the ribs may be used to position and/or engage the device within the body 20 and the ribs may be configured to provide a snap-fit. The device 300 may include a needle 306 which may already be coupled to the barrel 304, and if so, any safety caps may be removed and the needle 306 may be injected into a patient's body. In one embodiment, the needle 306 may arrive detached from barrel 304 and the needle 306 may be coupled to the barrel through connector 308 after the device 300 is mounted with the limiter 10. It should be recognized that the dispensing device 300 may not include a needle 306 and the medium may be expelled from the device 300. The patient or caregiver pushes the plunger 304 to slide the plunger a predetermined distance D in a dispensing direction A to thereby dispense medium. Medium may be dispensed until the plunger 304 contacts a stop 40 that is configured to prevent further movement of the plunger 304 in the dispensing direction. Thereafter, the device 300 and limiter 10 may be discarded.

As mentioned above, the limiter 10 is configured to limit the amount of medium dispensed from a dispensing device 300. In one embodiment, the medium is a medication, such as, but not limited to various drug therapies and/or antibiotics. In one embodiment, the limiter 10 may be used with Avonex® which is an Interferon beta-1a intramuscular injection used to prevent the symptoms of multiple sclerosis (MS) and may also slow the development of disability in patients with MS, which is manufactured by Biogen Idec. One of skill in the art would recognize that the invention is not limited for use with a dispensing device having a particular medium therein. As discussed above, the medium may, for example, be in liquid form, gaseous form, and/or a solid form (such as a powder form). It should also be recognized that the limiter may be used to limit the dispensing of other non-medication substances, as the invention is not so limited.

The limiters 10, 100, 200 are discussed above in combination with a prefilled dispensing device, such as, but not limited to a prefilled syringe. It should be appreciated that the limiters 10, 100, 200 may be used with a dispensing device that is manually filled, as the present invention is not limited for use with prefilled devices.

The limiter 10 may be made manufactured in a variety of ways as the invention is not so limited. In one embodiment, the stop 40 is integrally formed with the body 20. In another embodiment, the two components are formed separately and may thereafter be secured together by methods known to one of ordinary skill in the art such as, but not limited to adhesive, mechanical fasteners, or by welding. In one embodiment, the body 20 and stop 40 are made from molded plastic, and the limiter 10 may, for example be injection molded.

As mentioned above, and as shown in FIG. 1, a kit may be provided with a plurality of limiters 10, 100, 200 for limiting the amount of medium delivered from a dispensing device 300. Limiters 100, 200 may be configured to be substantially similar to the limiter 10 described above and shown in FIGS. 2-10. However, as shown in FIG. 1, the height $H_1$, $H_{12}$ $H_3$ of the stops 40, 140, 240 may vary. As mentioned above, by varying the height of the stop 40, one can control the predetermined distance D that the plunger 304 is permitted to travel in the dispensing direction, thus dispensing a controlled partial dose. In this illustrative embodiment, the first limiter 10 has the tallest stop 40 and is thus configured to provide the smallest dose of liquid. This first limiter 10 may be configured for the initial dose of the liquid to minimize side affects of the medication. In this illustrative embodiment, the third limiter 200 has the shortest stop 240 and thus, may be configured to provide a larger dose. The second limiter 100 has a stop 140 which is shorter than the first stop 40 but taller than the third stop 240, and thus is configured to provide a partial dose that is larger than the dose provided by the first limiter 10 and smaller than the dose provided by the third limiter 200. In one embodiment, the kit further includes a plurality of dispensing devices 300, and one dispensing device 300 may be provided for each limiter 10, 100, 200.

In one embodiment the limiter 10, 100, 200 is configured for a single use with one prefilled syringe and is designed to be disposable. It is also contemplated that the limiter 10, 100, 200 may be configured for reuse as the components of the limiter should not come into direct contact with the medium within the device 300 and may only contact the patient externally.

It should be appreciated that various embodiments of the present invention may be formed with one or more of the above-described features. The above aspects and features of the invention may be employed in any suitable combination as the present invention is not limited in this respect. It should also be appreciated that the drawings illustrate various components and features which may be incorporated into various embodiments of the present invention. For simplification, some of the drawings may illustrate more than one optional feature or component. However, the present invention is not limited to the specific embodiments disclosed in the drawings. It should be recognized that the present invention encompasses embodiments which may include only a portion of the components illustrated in any one drawing figure, and/or may also encompass embodiments combining components illustrated in multiple different drawing figures.

It should be understood that the foregoing description of various embodiments of the invention are intended merely to be illustrative thereof and that other embodiments, modifications, and equivalents of the invention are within the scope of the invention recited in the claims appended hereto.

The invention claimed is:

1. A limiter for a syringe, the limiter comprising:
   a single housing forming a receptacle constructed and arranged to mount with at least a portion of a syringe, the housing having a first end and a second end; and
   a stop integrally formed with and extending outwardly from the receptacle along a longitudinal axis of a dispensing direction, the stop being configured to permit movement of a plunger of the syringe a predetermined distance in the dispensing direction correlated to a desired volume of medium to be delivered from the syringe, wherein the stop is configured to prevent further movement of the plunger in the dispensing direction through direct contact of the stop with the plunger, thereby limiting an amount of medium delivered from the syringe to the desired volume of medium, wherein the limiter is configured to dispense only one desired volume of medium from the syringe.

2. The limiter of claim 1, wherein the stop is constructed and arranged as a collar extending outwardly from the first end of the housing, the collar having a channel therethrough, the collar being configured to receive at least a portion of the plunger such that the plunger is moveable within the channel.

3. The limiter of claim 2, wherein the collar is substantially C-shaped.

4. The limiter of claim 2, wherein the stop includes a socket configured to receive an end portion of the plunger.

5. The limiter of claim 4, wherein the socket is substantially C-shaped.

6. The limiter of claim 1, wherein the second end of the housing has an opening configured such that a needle of the syringe extends out of the housing.

7. The limiter of claim 1, in combination with a syringe.

8. The limiter of claim 1, further comprising a door pivotally coupled to the receptacle.

9. The limiter of claim 1, wherein the housing comprises at least one rib configured to retain the syringe within the housing.

10. The limiter of claim 9, wherein the at least one rib includes a first rib positioned at the first end of the housing and a second rib position at the second end of the housing.

11. The limiter of claim 1, wherein the housing includes at least one outwardly extending arm configured to provide a finger grip.

12. The limiter of claim 1, wherein the housing and stop are made from molded plastic.

13. A kit comprising:
   a plurality of limiters, including at least a first limiter as recited in claim 1, and a second limiter as recited in claim 1; and
   wherein the stop of the first limiter is configured to permit movement of the plunger a first predetermined distance in the dispensing direction and the stop of the second limiter is configured to permit movement of the plunger a second predetermined distance in the dispensing direction, wherein the first predetermined distance is greater than the second predetermined distance.

14. The kit of claim 13, further comprising a plurality of syringes.

15. A method of limiting the dispensing of liquid from a syringe, comprising:
   mounting a syringe with a limiter such that at least a portion of the syringe is mounted with a single housing forming a receptacle of the limiter, the housing having a first end and a second end, wherein a stop integrally formed with the receptacle extends from the receptacle;
   moving a plunger of the syringe a predetermined distance in a dispensing direction correlated to a desired volume of medium to be dispensed, to dispense the medium until the plunger contacts the stop that is configured to prevent further movement of the plunger in the dispensing direction through direct contact of the stop with the plunger, thereby limiting the amount of medium delivered from the syringe,
   wherein the limiter is configured to dispense only one desired volume of medium from the syringe.

16. The method of claim 15, wherein the act of mounting the syringe with a limiter includes placing the syringe in the housing and pivotally closing a door on the housing.

17. The method of claim 15, wherein the act of mounting the syringe with the limiter includes placing a plunger of the syringe in collar having a channel therethrough, such that the plunger is moveable within the channel.

18. The method of claim 15 wherein the act of mounting the syringe with the limiter includes retaining the syringe with at least one rib positioned on the housing.

* * * * *